United States Patent
Foote et al.

[19]

[11] Patent Number: 5,962,247
[45] Date of Patent: Oct. 5, 1999

[54] ASSAY FOR MICROORGANISMS AND DEVICE FOR USE THEREIN

[75] Inventors: Nicholas Peter Martin Foote, Cambridge; David Nelson, Cambs, both of United Kingdom

[73] Assignee: Celsis International PLC, United Kingdom

[21] Appl. No.: 09/068,255

[22] PCT Filed: Nov. 5, 1996

[86] PCT No.: PCT/GB96/02709

§ 371 Date: May 5, 1998

§ 102(e) Date: May 5, 1998

[87] PCT Pub. No.: WO97/17609

PCT Pub. Date: May 15, 1997

[30] Foreign Application Priority Data

Nov. 6, 1995 [GB] United Kingdom ............... 9522679

[51] Int. Cl.[6] .............. C12Q 1/42; C12Q 1/04; C12Q 1/00; G01N 33/53
[52] U.S. Cl. .............. 435/21; 435/34; 435/962; 435/963; 435/4; 435/283.1; 422/50; 422/68.1; 422/255; 422/256; 252/349
[58] Field of Search ................ 435/21, 34, 962, 435/963, 4, 283.1; 422/50, 68.1, 255, 256; 252/349

[56] References Cited

U.S. PATENT DOCUMENTS 1,469,221 10/1923 Kristofek et al. ............... 252/349
4,683,058 7/1987 Lyman et al. ............... 252/349

FOREIGN PATENT DOCUMENTS 1830229 1/1961 Germany.
9200317 1/1992 WIPO.

Primary Examiner—Louise N. Leary
Attorney, Agent, or Firm—Saliwanchik, Lloyd & Saliwanchik

[57] ABSTRACT

An assay device comprising a centrifugation tube and, as a sliding fit therein, a less deep inner tube whose base has one or more apertures sufficiently large to allow the passage of particles. This device can be used in an assay for microorganisms in a liquid sample containing fatty material, which comprises centrifuging the sample and a clearing agent in the device, removing the inner tube containing the fatty material, removing at least substantially all of the liquid supernatant in the centrifugation tube, and determining the presence of ATP in the sedimented pellet.

6 Claims, 1 Drawing Sheet

ASSAY FOR MICROORGANISMS AND DEVICE FOR USE THEREIN

FIELD OF THE INVENTION

This invention relates to an assay for microorganisms and to a device for use in such an assay.

BACKGROUND OF THE INVENTION

Rapid microbial testing by ATP bioluminescence demands assays that will work in a variety of sample matrices. The microorganisms can be determined by lysing them and measuring the light emitted in the presence of luciferase, as a function of the ATP contained in the microorganisms. However, before detection can take place, it is often necessary to separate the organisms from the remainder of the sample, which may contain contaminating amounts of ATP.

Separation of the microorganisms from their environment poses particular problems in aqueous samples also containing fatty material, e.g. milk. It has been proposed to centrifuge such samples with a clearing agent in a centrifugation tube, to give a pellet comprising the intact microorganisms, supernatant liquid and, above that, a fatty layer. The fatty layer and the liquid can be removed by aspiration, but the removal of fatty material is inefficient and time-consuming. It is also unsuited to ready use by unskilled personnel, e.g. for simple testing of samples of milk at a large dairy or distribution depot. If the sample is cream, which may contain 40% fat or more, the problems are greatly magnified and the technique of aspiration is not considered suitable.

Centrifugation tubes are known, which additionally comprise, as a sliding fit therein, a less deep inner tube whose base is a filter material. Sample is introduced into the tubes when fitted together, and centrifugation enhances filtration, leaving solids on the filter.

SUMMARY OF THE INVENTION

It has now been appreciated that, by slight adaptation of a centrifugation tube of the type described above, such that the base of the inner tube has one or more apertures sufficiently large to allow the passage of particles, the inner tube can be used to remove efficiently, not solids but rather a fatty deposit lying above an aqueous supernatant layer. Such a tube can therefore be used to solve the problems associated with the separation of microorganisms from cream. Aspiration is unnecessary. After the fatty material has been removed, supernatant liquid can be removed simply by decantation, although aspiration may be used if desired.

DESCRIPTION OF THE INVENTION

The term "centrifugation tube" is used herein merely to define the outer of the two mating tubes in a device of the invention. It may conveniently be provided with a tapering base in which a solid pellet is formed, on centrifugation. The inner tube is less deep, only in order to define a volume, beneath its base, in the centrifugation tube. This volume will be determined only by the need to ensure that, in a sample of a given amount, the fatty content will lie above its base, after separation of the sample, on centrifugation.

Unlike two-part centrifugation tubes of the type already known, the base of the inner tube according to the invention is adapted not to retain solids, and indeed to allow the passage of all components in the sample in either direction. It is thus used, not to cause separation during centrifugation, but only after centrifugation has caused separation into a solid pellet, and supernatant liquid and fatty layers.

The fatty layer is simply removed by taking out the inner tube, leaving the centrifugation tube containing solid material (including intact microorganisms) and supernatant liquid.

On removal of the inner tube, supernatant (aqueous) liquid drains through the aperture(s) in the inner tube. The layer of fatty material is sufficiently firm that it is retained by the inner tube, without immediately draining out, and can be disposed of separately.

The liquid can now be poured off. In order to remove liquid completely, aspiration may be used, but an equally effective way of ensuring that any liquid remaining after decantation does not affect the result is to add an ATPase. Microorganisms in the solid pellet can now be assayed by conventional means, e.g. by bioluminescence.

ATPase may be added after removal of the fatty material, and preferably after decantation of liquid. The material in the centrifugation tube may be transferred to a cuvette that fits in a luminometer. ATPase may be incorporated in reagent added to resuspend the pellet, and sufficient time allowed before bioluminescence assay for the non-microbial ATP to be hydrolysed.

Alternatively, and especially if the centrifugation tube is itself to be used as the cuvette, ATPase may be incorporated in reagent added to the sample before centrifugation. For example, it may be added with a clearing agent, i.e. any material (examples of which are known) that associates with microorganisms in the sample and enhances their separation from the liquid and fatty phases, on centrifugation.

The one or more apertures in the base of the inner tube are sufficiently large to allow the passage of any components in the sample, during centrifugation. For example, the minimum dimension of the or each aperture is at least 1 mm and more preferably at least 6 mm.

BRIEF DESCRIPTION OF DRAWINGS

The invention will now be illustrated by way of example with reference to the accompanying drawings, in which:

FIGS. 1A and 1B show a device comprising a centrifugation tube 1 and an inner tube 2 that is a sliding fit in the centrifugation tube. The centrifugation tube has a tapering base 3. The inner tube is open at its base 4 (alternatively, the base may comprise a coarse grid or array of holes). A closure member 6 is hingedly attached to the centrifugation tube, and serves to close either tube.

FIGS. 2A, 2B and 2C show the same device as FIGS. 1A and 1B. They show additionally a solid pellet 7, supernatant liquid 8 and fatty material 9, that have been separated by centrifugation. FIGS. 2B and 2C show separation of the fatty material by removal of the inner tube 2.

The following Example illustrates the invention.

EXAMPLE (and Comparative Example)

A freshly-pasteurised cream sample was split into two portions: one was stored at 4° C. ("clean cream") whilst the other was allowed to spoil by storage overnight at room temperature ("spoiled cream"). Serial dilutions were then made of spoiled cream in clean cream to give a range of microbial counts from $1.5 \times 10^2$ cfu/ml to $7.6 \times 10^6$ cfu/ml according to standard plate counts. The samples were each assayed by two methods.

Method 1 (aspiration) used reagents from a commercially-available milk assay kit ("Enliten" Milk Total Viable Organisms Assay from Promega Corporation, Madison, U.S.A.). The procedure was as instructed for milk testing: 1 ml cream sample was mixed in a conventional microcentrifuge tube with 0.5 ml of reagent A, a clearing agent. The mixture was centrifuged at 10,000 rpm for 5 minutes. The thick fatty upper layer and liquid supernatant were then carefully removed by aspiration under suction, and the remaining pellet was resuspended in 0.1 ml of Transfer Reagent and transferred to the bottom of a cuvette. After 2 minutes the cuvette was placed in an Optocomp I luminometer (Celsis Ltd., UK) and the bioluminescence assay performed by automatically injecting 0.1 ml of extractant, followed by a 10 second delay and the injection of 0.1 ml of luciferase/luciferin reagent. The resulting light was integrated for 10 seconds and the result recorded as a RLU (relative light unit) figure.

Figure 1A:
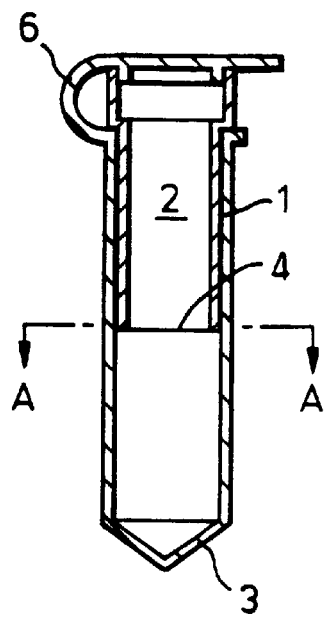
FIG. 1A is a side sectional view of an embodiment of this invention (approximately actual size)
Figure 1B:
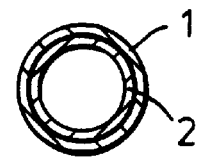
FIG. 1B is a sectional view of the device shown in FIG. 1A along the line A—A.
Figure 2A:
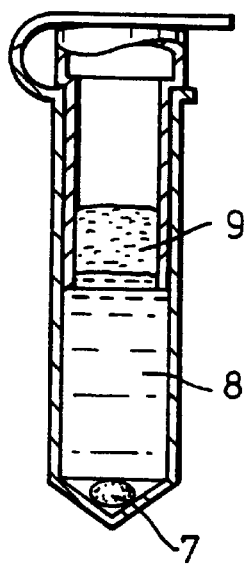
FIG. 2A shows the device of FIG. 1A including a sample of cream that has been centrifuged.
Figure 2B:
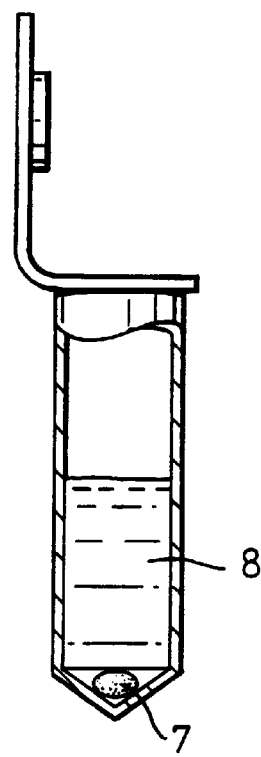
FIGS. 2B and 2C show the embodiment of FIG. 2A after separation of its two component tubes.
Figure 2C:
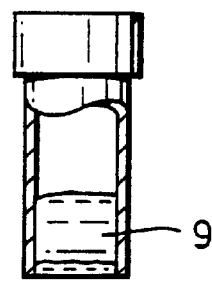

Method 2, the method of the invention, followed the same procedure with the following exceptions. Firstly, centrifugation was performed in a microcentrifuge tube containing a hollow tube insert as shown in FIG. 1. Secondly, the aspiration step was omitted. Instead, after centrifugation, the fatty layer was removed by simply withdrawing the inner tube and the liquid supernatant was decanted. The final drop of liquid was removed by touching the rim of the microcentrifuge tube against a paper tissue. Thirdly, ATPase (Celsis Ltd., UK) at 0.1 U/ml was included in the transfer reagent. All timings and volumes were identical in the two methods.

Results are given in the Table below.

| cfu/ml in cream sample | RLU Method 1 | RLU Method 2 |
| --- | --- | --- |
| $1.5 \times 10^2$ | 36720 | 7613 |
| $7.0 \times 10^3$ | 34299 | 8075 |
| $6.5 \times 10^4$ | 82868 | 17416 |
| $7.3 \times 10^5$ | 406684 | 189449 |
| $7.6 \times 10^6$ | 3098949 | 2348635 |

At low microbial levels, method 2 clearly gives lower signals because of the more efficient removal of non-microbial ATP by incorporation of the ATPase. At higher levels of contamination, method 2 also gives lower RLU values, probably because the added ATPase tends to destroy some of the released microbial ATP before it can react with luciferase to cause light emission. Overall, however, neither linearity nor sensitivity of the assay is compromised by use of the more convenient and robust method of the invention.

Note that other commercially-available extractants, luciferase-luciferin reagents and transfer reagents can be substituted. Some extractants are especially effective at inactivating ATPase and may therefore give higher signals from microbial ATP.

We claim:

1. A method of separating fatty material in a centrifuged sample, from sedimented pellet and supernatant liquid, by placing said sample in an assay device wherein said method comprises use of an assay device comprising a centrifugation tube and, as a sliding fit therein, a less deep inner tube whose base has one or more apertures sufficiently large to allow the passage of particles; and recovering said fatty material.

2. An assay for microorganisms in a liquid sample containing fatty material, which comprises centrifuging the sample in a device comprising a centrifugation tube and, as a sliding fit therein, a less deep inner tube whose base has one or more apertures sufficiently large to allow the passage of particles, removing the inner tube containing the fatty material, removing at least substantially all of the liquid supernatant in the centrifugation tube, and determining the presence of ATP in the sedimented pellet as indication of the presence of microorganisms.

3. The assay according to claim 2, which comprises adding an ATPase to the sample before centrifugation.

4. The assay according to claim 2, which comprises adding an ATPase to the sample after removing the liquid supernatant.

5. The assay according to claim 2, in which the sample is dairy cream.

6. The assay, according to claim 2, wherein a clearing agent is centrifuged with said sample.

* * * * *

UNITED STATES PATENT AND TRADEMARK OFFICE
CERTIFICATE OF CORRECTION

PATENT NO. : 5,962,247
DATED : October 5, 1999
INVENTOR(S) : Nicholas Peter Martin Foote, David Nelson It is certified that error appears in the above-identified patent and that said Letters Patent is hereby corrected as shown below:

Column 4, line 35 (Claim 2): "as indication" should read --as an indication--.

Signed and Sealed this

Ninth Day of May, 2000

Attest:

Q. TODD DICKINSON

Attesting Officer

Director of Patents and Trademarks